United States Patent [19]

Spaulding et al.

[11] Patent Number: 5,945,338
[45] Date of Patent: Aug. 31, 1999

[54] METHOD AND APPARATUS FOR AUGMENTING MASS TRANSFER IN A ROTATING CELL CULTURE SYSTEM

[75] Inventors: Glenn F. Spaulding; Mike Zerkus, both of Houston, Tex.

[73] Assignee: VivoRx Pharmaceuticals, Los Angeles, Calif.

[21] Appl. No.: 08/670,363

[22] Filed: Jun. 26, 1996

Related U.S. Application Data

[60] Provisional application No. 60/000,507, Jun. 26, 1995.

[51] Int. Cl.$^6$ ............................... C12N 5/02; C12M 3/02
[52] U.S. Cl. .................... 435/394; 435/286.7; 435/298.2
[58] Field of Search ........................................ 435/383, 394, 435/395, 403, 286.6, 286.7, 298.2, 304.1, 818

[56] References Cited

U.S. PATENT DOCUMENTS

| | | |
|---|---|---|
| 4,391,912 | 7/1983 | Yoshida et al. . |
| 4,554,499 | 11/1985 | Sherman et al. ........................ 318/696 |
| 4,749,654 | 6/1988 | Karrer et al. . |
| 4,829,811 | 5/1989 | Ehlert et al. ................................ 73/59 |
| 4,948,728 | 8/1990 | Stephanopoulos et al. .............. 435/41 |
| 4,962,033 | 10/1990 | Serkes et al. . |
| 4,988,623 | 1/1991 | Schwarz et al. . |
| 5,026,650 | 6/1991 | Schwarz et al. . |
| 5,037,378 | 8/1991 | Muller et al. ............................ 600/36 |
| 5,057,428 | 10/1991 | Mizutani et al. . |
| 5,104,802 | 4/1992 | Rhodes et al. ....................... 435/298.2 |
| 5,153,131 | 10/1992 | Wolf et al. . |
| 5,155,034 | 10/1992 | Wolf et al. . |
| 5,330,908 | 7/1994 | Spaulding . |
| 5,347,998 | 9/1994 | Hodson et al. . |
| 5,437,998 | 8/1995 | Schwarz et al. ..................... 435/298.2 |
| 5,516,692 | 5/1996 | Berndt ................................. 435/286.7 |

FOREIGN PATENT DOCUMENTS 0 164 888  12/1985  European Pat. Off. ............ 435/298.2

*Primary Examiner*—William H. Beisner
*Attorney, Agent, or Firm*—Gray, Cary, Ware & Freidenrich, LLP; Stephen E. Reiter

[57] ABSTRACT

A horizontally rotating cell culture system with enhanced oxygenation is described. The system achieves greater oxygenation through the use of a multiphase motor and non-linear acceleration/deceleration, to disrupt the establishment of boundary layers.

4 Claims, No Drawings

METHOD AND APPARATUS FOR AUGMENTING MASS TRANSFER IN A ROTATING CELL CULTURE SYSTEM

RELATED APPLICATIONS

This application claims the benefit of U.S. Provisional Application No. 60/000,507, filed Jun. 26, 1995, the entire contents of which are hereby incorporated by reference herein.

FIELD OF THE INVENTION

The present invention relates to novel means for increasing the mass transfer in a rotating cell culture system. By using a stepper motor or other multiphase motor, non-linear rotation can be achieved such that the sum of the angular acceleration and deceleration vectors is zero. The invention provides a low cost and universally useful means for improving mass transfer in rotating culture systems.

BACKGROUND OF THE INVENTION

The culture process of mammalian cells, animal cells, insect cells, bacteria, yeast and molds has one major rate limiting step, oxygen mass transfer. Oxygen metabolism is essential for metabolic function. In mammalian and animal cell culture it is especially important during the early stages of rapid cell division. Oxygen utilization per cell is greatest when cells are suspended; requirements decreasing as the cells aggregate and differentiate. However, during the later phases of cell culture, as the number of cells per unit volume increases, the bulk oxygen mass transfer requirements increase. Traditionally, increased requirements are accommodated by mechanical stirring methods. However, these methods create fluid shear gradients that can damage cellular growth.

There are several basic strategies for increasing the gas mass transfer across a membrane: increase oxygen concentration; increase the rate of transfer from the air to the media; and/or increase the surface area for gas exchange. Increasing the oxygen partial pressure will increase the bulk oxygen transfer. However, a boundary layer of oxygen toxicity will form at the gas permeable membrane-media interface. Cells entering the toxic boundary layer could sustain irreparable damage.

Approaches to increasing the rate of gas transfer at the air-membrane-media interface include: increase the rate of air movement across the membrane with air pumps or other mechanical means; increase the gas diffusion rate across the membrane by selecting a more gas permeable membrane; and/or increase the rate of media flow past the membrane. In each approach, the rate of exchange across the gas permeable membrane is augmented, leading to improved gas exchange.

The third approach for increasing bulk gas transfer is to increase the air-membrane-media surface area. An enlarged surface enhances the bulk gas transfer. Improved gas exchange serves to both increase oxygen availability and remove the carbon dioxide by-product.

Each of the above-described potential means for increasing gas mass transfer in cell cultures is either detrimental to the cells in the culture medium, and/or requires substantial modification of the apparatus and/or medium employed for culture. Accordingly, there is still a need in the art for simplified, readily implemented means to improve gas mass transfer in cell culture.

PRIOR ART

Prior art of possible relevance to the present invention includes the following patents and the references ted therein:

U.S. Pat. No. 5,437,998 issued to R. P. Schwartz et al. on Aug. 1, 1995, relates to the use of a specifically designed rotating cell culture vessel which is constructed of materials which are permeable to oxygen and carbon dioxide.

U.S. Pat. No. 5,330,908 issued to G. F. Spaulding on Jul. 19, 1994, relates to horizontally rotating a cell culture vessel at constant angular velocity.

U.S. Pat. No. 5,153,131 issued to D. A. Wolf et al. on Oct. 6, 1992, relates to horizontally rotating a cell culture vessel at constant angular velocity.

U.S. Pat. No. 5,057,428 issued to S. Mizutani et al. on Oct. 15, 1991, relates to horizontally rotating a cell culture vessel at constant velocity.

U.S. Pat. No. 5,026,650 issued to R. P. Schwartz et al. on Jun. 25, 1991, relates to horizontally rotating a cell culture vessel at constant angular velocity.

U.S. Pat. No. 4,988,623 issued to Schwarz et al. on Jan. 29, 1991, relates to both inner and outer housings rotated by a motor to minimize the shear at boundary layers.

U.S. Pat. No. 4,962,033 issued to J. M. Serkes on Oct. 9, 1990, is an example of a cell culture roller bottle rotated at constant angular velocity.

U.S. Pat. No. 4,948,728 issued to G. Stephanopauous et al. on Aug. 14, 1990, discloses a porous ceramic material with a plurality of flow passages.

U.S. Pat. No. 4,749,654 issued to D. Karrer et al. on Jun. 7, 1988, relates to a cell growth system using gas permeable membranes and a waste gas removal system. A stirrer is used for agitation.

U.S. Pat. No. 4,391,912 issued to K. Yoshida et al. on Jul. 5, 1983, is an example of a cell culture system with hollow fibers that is not rotated.

Each of the above-referenced patents are hereby incorporated by reference herein in their entirety.

SUMMARY OF THE PRESENT INVENTION

In accordance with the present invention, a multiphase motor (e.g., a stepper motor) is disposed to a shaft that horizontally rotates a cell culture chamber to suspend cells. The multiphase motor contemplated for use herein is controlled by commonly available electronic components, as is known in the art. Stepping is achieving by sequentially activating the phase windings of the motor. Steps can be full steps, half steps or microsteps.

In the case of a stepper motor, the square wave that energizes the coils can be rounded by conventional capacitive and active components. Rounding an energizing square wave is used to control the rate of acceleration and deceleration. Acceleration and deceleration in non-stepping motors can be achieved by adjusting the phasing of coils.

The resulting cells produced employing invention methods form larger cellular aggregates than are produced employing prior art methods.

DESCRIPTION OF THE PREFERRED EMBODIMENT

The apparatus and method of the present invention enable improved gas mass transfer rates across the air-membrane-media and cell-media boundary layers in rotating cell culture systems. A stepper motor (e.g., 3.75°/step) is disposed to the shaft of a horizontally rotating cell culture vessel. Square wave pulses are generated by an integrated circuit (e.g., UNC5804B). The pulse rate is controlled by an operator to achieve the desired revolutions per minute (RPM). On each wire lead to the stepper motor is a capacitor. The capacitance value of each capacitor employed can range from 100 picofarads (pf) to 10 farads.

Suitable capacitance values are chosen by placing an oscilloscope across the capacitor and observing the rounding of the wave form. Larger capacitors result in the greatest rounding. As the square wave approaches the shape of a sine wave, acceleration and deceleration approaches zero. The more square the corners of the square wave, the greater the boundary layer disruption.

To determine oxygen requirements, a sample of cell culture media is withdrawn from an actively growing culture. The sample is tested for dissolved oxygen using conventional means, e.g., a conventional blood gas analyzer. As the oxygen levels fall in the cell culture chamber, the size of the capacitor is reduced. Typically, when media oxygen falls below 40 mm Hg, the capacitance is decreased by a multiplier of 10.

Stepper motors and multiphase motors can adjust their angular acceleration during each revolution or from revolution to revolution. Stepper motors are especially suited to accelerate to a position then stop at specified position. Thus, the angular velocity vectors sharply increase, then decrease. In a constant RPM mode, the stepper motor accelerates to the next position stop, then when the next phase is energized accelerates to the next position. The RPM remains constant, however the motor is incrementally stepped to each position, and undergoes a cycle of acceleration followed by deceleration. The net sum of the angular acceleration and deceleration is zero, and the RPM is constant.

While not wishing to be bound by any theory, it is presently believed that fluid in an accelerating/decelerating cell culture chamber will not accelerate or decelerate in phase with the structural portion of the chamber. Moreover, the cells suspended in the chamber will not match the acceleration or deceleration phases of the structural portion of the chamber. Consequently, boundary layers near oxygenating surfaces and surrounding cellular growths are disrupted. Since the net sum of the acceleration/deceleration vectors is zero, the cells remain in suspension, while boundary layers are perturbated. Perturbating boundary layers decreases the oxygen gradient that metabolically active cells create, thereby improving the mass transfer to the cell, and enabling the production of desirably large cellular aggregates.

It will be apparent to those skilled in the art that various changes may be made in the invention without departing from the spirit and scope thereof, and therefore, the invention is not limited by that which is disclosed in the specification, but only as indicated in the appended claims.

That which is claimed:

1. A method for improving mass transfer in a rotating culture system, said method comprising:

subjecting the cell culture vessel of said rotating culture system to non-linear rotation such that the sum of the angular acceleration and deceleration vectors is zero, wherein the rotation of said cell culture vessel is controlled by a multiphase motor, and the multiphase motor is controlled by square wave pulses, and wherein rounding of the wave form of said wave pulses is controlled by a capacitor and the value of said capacitor falls in the range of about 100 picofarads up to 10 farads.

2. A method for improving mass transfer in a rotating culture system, said method comprising:

subjecting the cell culture vessel of said rotating culture system to non-linear rotation such that the sum of the angular acceleration and deceleration vectors is zero, wherein the rotation of said cell culture vessel is controlled by a multiphase motor, and the multiphase motor is controlled by square wave pulses, and wherein rounding of the wave form of said wave pulses is controlled by a capacitor and the value of said capacitor falls in the range of about 100 picofarads up to 10 farads; and monitoring the oxygen level of said cell culture media, and adjusting the size of the capacitor used for rounding the wave pulse in response thereto.

3. In a process for carrying out a rotating culture, the improvement comprising:

subjecting the cell culture vessel of said rotating culture system to non-linear rotation such that the sum of the angular acceleration and deceleration vectors is zero, wherein the rotation of said cell culture vessel is controlled by a multiphase motor, and the multiphase motor is controlled by square wave pulses, and wherein rounding of the wave form of said wave pulses is controlled by a capacitor and the value of said capacitor falls in the range of about 100 picofarads up to 10 farads; and monitoring the oxygen level of said cell culture media, and adjusting the size of the capacitor used for rounding the wave pulse in response thereto.

4. In a rotating cell culture apparatus, the improvement comprising:

placing a horizontally rotatable cell culture vessel of said rotating culture system in operational communication with a multiphase motor;

wherein the rotation of said cell culture vessel is controlled by the multiphase motor, and the multiphase motor is controlled by a controller which produces square wave pulses, and wherein rounding of the wave form of said wave pulses is controlled by a capacitor and the value of said capacitor falls in the range of about 100 picofarads up to 10 farads.

* * * * *